United States Patent [19]

Godard

[11] Patent Number: 5,341,181
[45] Date of Patent: Aug. 23, 1994

[54] SYSTEMS AND METHODS FOR CAPTURING AND PRESENTING VISUAL INFORMATION

[76] Inventor: Roger R. Godard, Van Beuren Rd., Morristown, N.J. 07690

[21] Appl. No.: 979,609

[22] Filed: Nov. 20, 1992

[51] Int. Cl.$^5$ .............................................. A61B 3/10
[52] U.S. Cl. ...................... 351/210; 351/209
[58] Field of Search ............. 351/209, 210, 211, 205, 351/206

[56] References Cited

U.S. PATENT DOCUMENTS

| | | | |
|---|---|---|---|
| 3,804,496 | 4/1974 | Crane et al. | 351/210 |
| 4,544,246 | 10/1985 | Crane et al. | 351/211 |
| 4,755,045 | 7/1988 | Borah et al. | 351/210 |

FOREIGN PATENT DOCUMENTS 0456166  11/1991  European Pat. Off. ............ 351/209

*Primary Examiner*—Loha Ben
*Attorney, Agent, or Firm*—David P. Gordon

[57] ABSTRACT

A method for capturing and presenting a pattern of visual information includes tracking the movement of an observer's eye while imaging images in response to the observer's eye movement, transmitting the images to an image display, tracking the movement of a perceiver's eye and displaying the images in response to the perceiver's eye movement while fixing the image on the retina of the perceiver. A system for capturing a pattern of visual information includes an observer's eye movement tracker and an imager responsive to the observer's eye movement tracker. Images captured by the imager can be transmitted to a display or recorded for later display. A system for presenting a pattern of visual information includes a display, a perceiver's eye movement tracker and an image fixer. Images from the imager or recorded images captured by the imager are displayed in response to the perceiver's eye movement tracker and fixed on the retina of the perceiver by the image fixer.

15 Claims, 3 Drawing Sheets

SYSTEMS AND METHODS FOR CAPTURING AND PRESENTNG VISUAL INFORMATION

BACKGROUND OF THE INVENTION

This invention broadly relates to systems and methods for capturing and presenting visual information. More particularly, the invention relates to systems and methods for allowing a viewer to see images in the same manner that they are seen by another viewer. While not limited thereto, the systems and methods are applicable for training an individual who will be required to make ostensibly subjective visual determinations to make those determinations in the same or similar manner as made by an expert. Other applications include entertainment, research, therapy and the creation of art.

The visual system of the human eye can be considered to consist of an optical component which focuses a scene upon the retina, and a neural processing component which detects visual features of the scene and assembles a perception embedding meaning. Extensive research has demonstrated that the neural system, from the retina on, processes what is in essence a series of stills to create a perception which contains apparently continuous motion and change. Effectively, then, the vision system operates in a manner quite analogous to a moving picture (movie) which is comprised of a sequence of still photographs.

The neuromuscular system of the eye operates to cause the eye to track points of interest in the visual field, i.e., the scene, and to focus the points of interest in the fovea, the small region of extremely high resolving capacity in the retina. The tracking of the eye, however, is not continuous. Instead, tracking is in the form of a sequence of extremely quick jumps (saccades), which separate longer periods (fixations) during which the eye does not move and the focused scene is fixed in place on the retina. The vision system appears to be sensitive to information only during fixations. Information presented during saccades is not perceived, while the same information presented for the same duration during a fixation period is perceived.

Besides the saccadic movement of the eye, there is another finer level of eye movement called nystagmus, which continuously makes low amplitude jumps essentially at random. The effect of nystagmus is to cause the point focused in the fovea of the retina to jitter, while still staying within the high resolution area. The primary purpose of nystagmus appears to be to prevent saturation and exhaustion of individual receptor cells in the retina. Subsequent post-retinal neural processing completely removes the motions induced by nystagmus from the perceived scene. Motions induced by saccades are largely removed as well, although, to a limited extent, the saccadic motion removal is under conscious control.

Certain well known research findings are key to the hereinafter described invention. See, e.g., Monty, Richard A. and Senders, John W., *Eye Movements and Psychological Processes*, John Wiley & Sons (1976). First by optical tracking of the eyeball it is possible to detect where within a scene an eye is gazing from saccade to saccade, and even from jitter to jitter of nystagmus. See, e.g., Frecker, R. C. et al, *High-Precision Real-Time Measurement of Eye Position Using the First Purkinje Image*, Theoretical and Applied Aspects of Eye Movement Research, Elsevier Science Publishers B.V. (1984). Second, individuals are found to use idiosyncratic scanning patterns as they saccade over a scene. The patterns apparently depend on the scene content and the emotional state and predispositions of the subject. Third, a device which tracks eye motions at the saccade or nystagmus level is commonly called a tracker and such trackers are well known and in wide commercial use today, for example in aircraft simulators. Fourth, it is known that a tracker can be coupled to an optical apparatus called a fixer which projects a spot of light or other visual object and moves the spot in precise step with the eye movements detected by the tracker in such a way that the spot is always focused on exactly the same place on the retina, i.e. the fovea, regardless of the motions of the eye. Subjects find that the spot rapidly drops from perception and becomes effectively invisible. Fixers are in commercial use today, for example in laser surgery of the retina.

SUMMARY OF THE INVENTION

It is a primary object of the invention to utilize trackers and fixers to provide systems and methods which allows a perceiver to see images in the same manner as they are seen by another viewer (the observer); i.e., "to see through the eyes of the observer." With the provided systems and methods, a novice can view an object or scene in the manner it is viewed by an expert.

In accord with the object of the invention, a system is provided for providing a projection of a pattern of visual observation, i.e. information, on a retina of a person who is to perceive the pattern (perceiver), the pattern being a replica of a pattern of visual information which has previously excited or is presently exciting the retina of another gazing individual (observer). The system broadly comprises a tracking means for tracking the eye movement of the observer as the observer visually inspects the image(s) of interest. Moveable imaging means responsive to the tracking means produce an image of the pattern location on which the eye of the observer has focused in the fovea of the retina, and this image is directed to a recording means which produces a record of received images or the image is directed to a projector means. A projector means is provided in the system for projecting the aforedescribed previously recorded pattern or for projecting the pattern in real time for viewing by the perceiver. Tracking means for tracking the eye movement of the perceiver are provided, and moveable imaging means, responsive to the eye tracking means of the perceiver are provided to present the images projected by the projector means to the retina of the eye of the perceiver. With the provided system, the perceiver will eventually lock onto the images provided by the system such that the perceiver will feel himself to be looking through the observer's eyes.

The system may include recording means for recording the pattern of visual information from the observer for viewing by the perceiver at a later time or the system may operate in real time. Moreover, recorded patterns may be edited or combined with other patterns and patterns may be synthesized in a manner analogous to computer generated animation.

Additional objects and advantages of the invention will become apparent to those skilled in the art upon reference to the detailed description in conjunction with the accompanying drawings.

BRIEF DESCRIPTION OF THE DRAWINGS

FIG. 1A shows a detailed drawing of the lens and a portion of the camera as indicated in the circular indication of FIG. 1;

FIG. 2A shows a detailed drawing of the eyeball of FIG. 2 in several positions.

DETAILED DESCRIPTION OF THE PREFERRED EMBODIMENT

Figure 1:
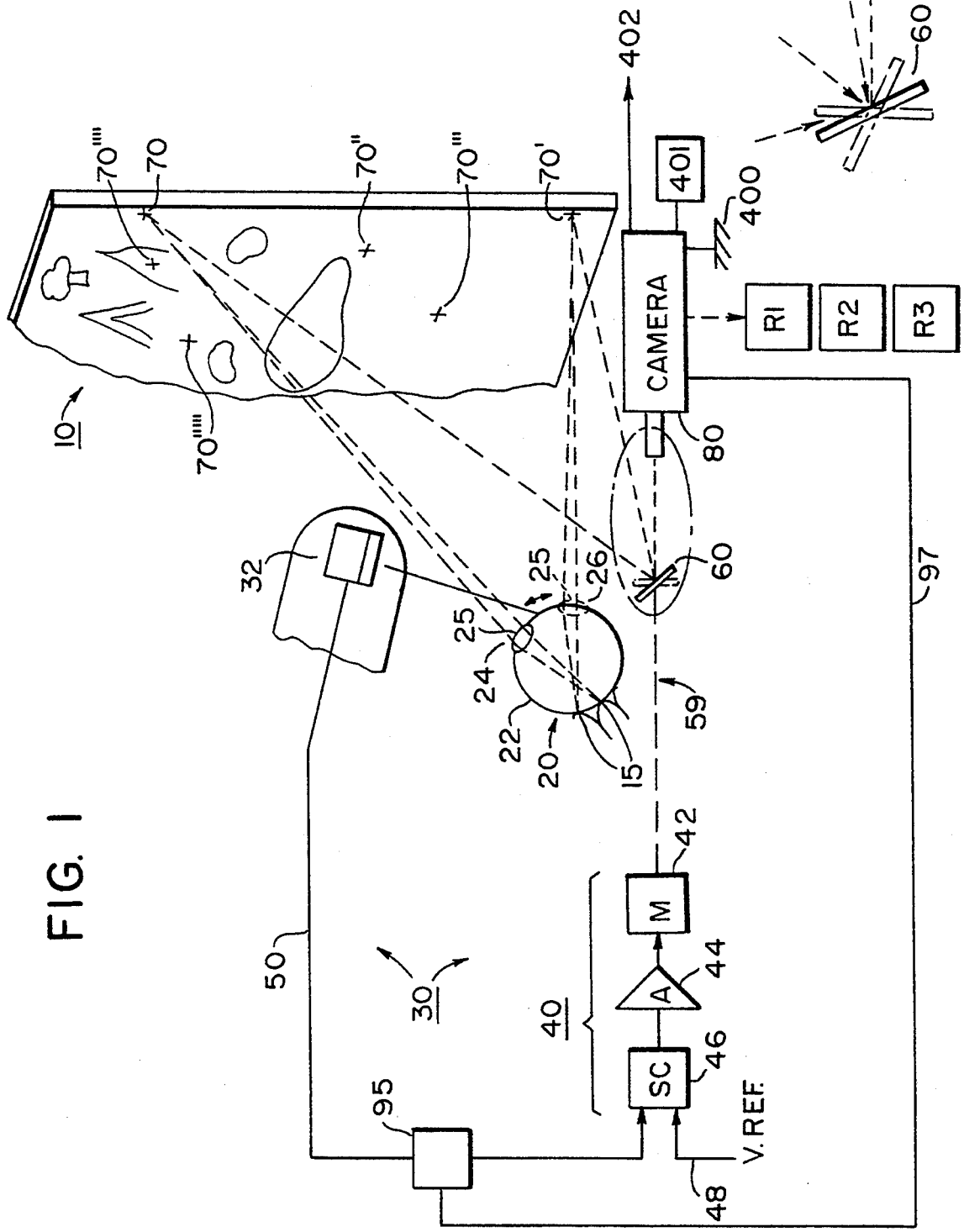
FIG. 1 shows a schematic illustration of a subsystem of the system of the present invention which obtains and records the images viewed by the observer.

The invention involves use of two subject individuals: a gazer or observer; and a perceiver. The observer gazes at some scene of interest and a record of what the observer observes is obtained. Subsequently the recorded scene is presented to a perceiver so that the perceiver, in effect looks at the recorded scene in precisely the same way as the observer did, saccades and all. Alternatively, the record is presented to the perceiver simultaneously in real-time.

To achieve the effect described, it is required that both the observer and the perceiver have their spontaneous eye motions tracked. The observer's eye motions are tracked in order to determine where on the scene the observer is looking between saccades. The perceiver's eye motions, on the other hand, are tracked in order to remove the perceiver's own eye movements, so that the recorded scene containing the observer's eye movements may be presented to an effectively immobile perceiver retinas.

The system of the invention includes two subsystems: one for the observer; and one for the perceiver. For the observer, as will be described in more detail hereinafter, the subsystem comprises a tracker and a camera type device which are servo linked so that the point of the scene which the observer's eye focuses on the fovea of his retina is always located at the center of the camera image, regardless of the observer's eye motion. For the frame by frame record captured by the camera in such an apparatus, the center of each frame corresponds to the point in the scene at which the observer was gazing at the moment of frame capture. If the captured record is projected like a movie on a screen, it would be nearly impossible to make sense of the record since the screen image would jump around significantly.

The perceiver's sub-system comprises a fixer of the type noted above. However, instead of fixing a spot of light to one point of the perceiver's retina i.e., the fovea, it fixes a projection of the record from the camera on the fovea of the perceiver's retina The fixing optics of the fixer are arranged so that the center of the recorded camera image is fixed on the fovea of the perceiver. The fixer thus eliminates the perceiver's own eye movements. Consequently, the image which is projected on the perceiver's retina corresponds only to the eye movements of the original observer. The actual pattern of cell stimulation on the retina of the perceiver is exactly the same as the pattern of stimulation undergone by the retina of the observer.

Initially a new perceiver using the apparatus of the invention may perceive an extremely jumpy image. This subjective effect is extremely disorienting. However, the neural processing of the brain appears to be able to compensate for the lack of correlation between the perceiver's eye muscle movements and the movement of the image on the retina. After a period of adaptation, the perceiver seems to suddenly lock in the record, in a manner quite similar to the sudden perception of three dimensions that occurs after staring for a while at a stereogram. The subjective effect is that the perceiver suddenly feels himself to be looking through the observer's eyes.

It is a truism in art education that the thing to learn is how to look. This invention permits a student to look at a scene or work of art, but literally through the eyes of a master. Other applications range from entertainment to forensics.

With reference to FIGS. 1 and 1A, a pattern of visual information is indicated at 10, which can be, for example, a portrait or landscape painting, a moving image (movie), or a view of reality. In FIG. 1, an eye 20 of a gazing individual is shown with a retina 22 a fovea 15 of the retina (the small region of high resolving capacity), and a pupil 25. In FIG. 1, two different positions 24, 26 are shown for the eye 20, although it will be appreciated that the eye can take an effectively unlimited number of positions.

In accord with the invention, an eye movement tracking means 30 of known type is provided. The tracking means 30 includes an eye movement photo sensor 32 which is electrically connected to a conventional servo system 40. Servo system 40 includes servo motor 42, power amplifier 44, and a conventional servo controller 46 to which is applied the customary reference voltage 48. Upon detection of eye movement of eye 20 by photo sensor 32, an electrical signal is applied over line 50 to servo controller 46. In response, a signal is sent to amplifier 44 which provides a feedback signal to motor 42 which causes (via mechanical coupling at 59) an imaging device, e.g., a pivotally mounted, mirror 60 to move. The imaging mirror may be moved by any adequate servo mechanism such as stepper motors or voice coils. In this manner, mirror 60 reflects a series of images 70, 70', 70'' . . . 70''''' which relate exactly to what is seen by the eye 20 of the observer. These images are presented directly to the camera 80, e.g. a film camera or a video camera, which makes records R1, R2, R3, . . . of the images on which observer's eye 20 has focused.

If desired, in the case of a stationary scene, it is possible to record the eye movements only and to record the image of the scene later using the recorded eye movements to direct the imaging mirror to capture the images of the stationary scene.

If desired, a discriminator or processor 95 can be provided in conjunction with the camera 80. With the discriminator, the motor 42 can be limited to respond only to the saccades of the eye 20 (as opposed to nystagmus). Also, by coupling the processor 95 via line 97 to the camera, records made by the camera 80 can be limited to those obtained during the fixation periods between saccades when the focused scene is fixed in place on the retina 22 of eye 20. The records (recording) R1 . . . Rn of the camera are preferably stored on a common film substrate 400 or on video tape 401 or other electronic storage or they are transmitted 402 "live" to the perceiver subsystem.

Figure 2:
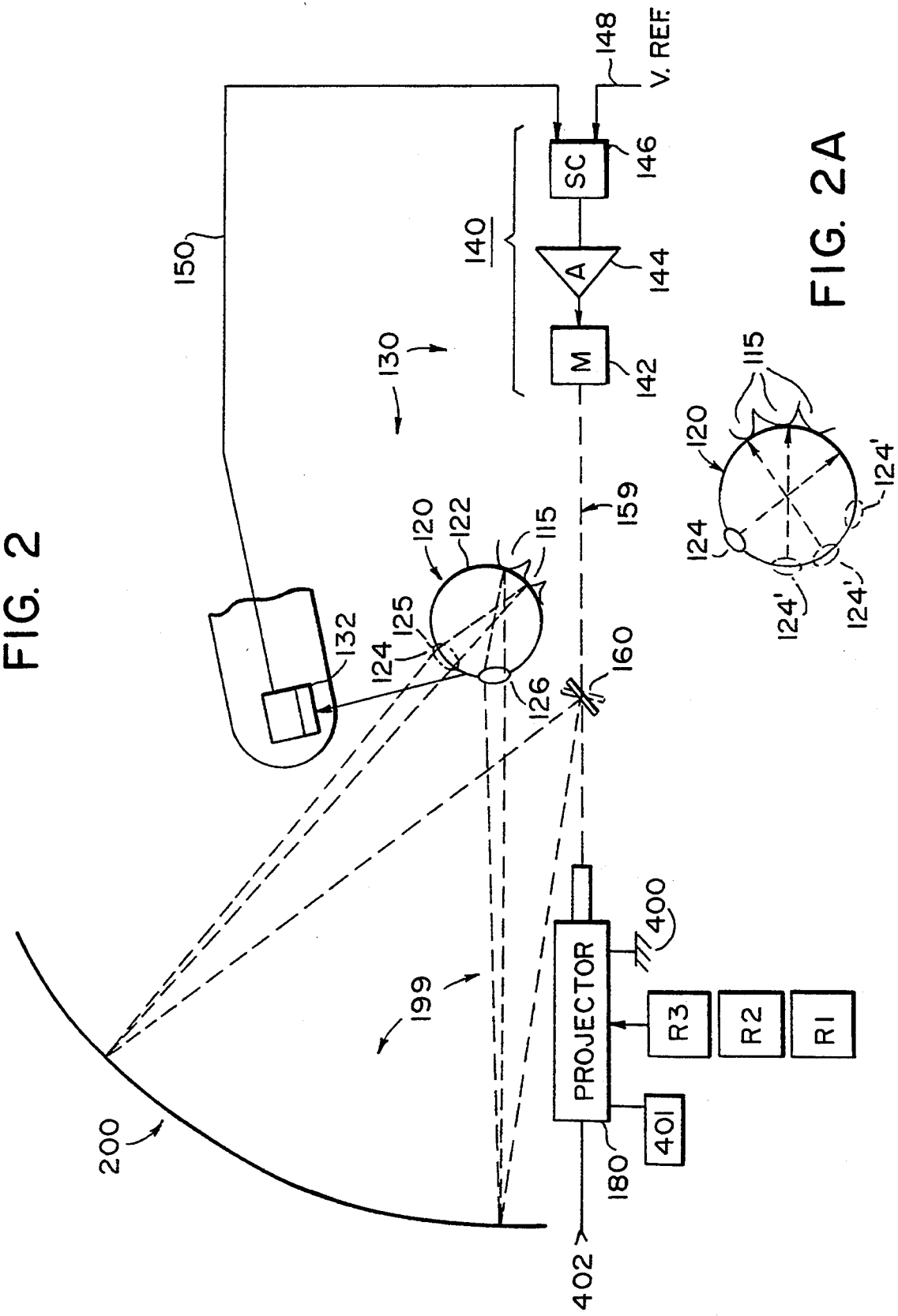
FIG. 2 shows a schematic illustration of a second subsystem of the system of the present invention which provides the recorded images to the perceiver.

Turning to FIGS. 2 and 2A, the subsystem of the perceiver is seen. The image records R1 . . . Rn are supplied to a projector 180 which is suitably of the known and commercially available type and which provides images of the records to pivotally mounted imaging means, e.g. mirror 160. Optionally, the image records may be supplied to a non-optical or electronic pixel display, thereby avoiding the need for mechanically operated imaging mirror 160. The eye 120 of a record perceiving individual is shown with the perceiver's retina 122, fovea 115, and pupil 125. Two different positions 124, 126 are shown for the perceiving individual's eye 120. An eye movement tracking means 130 of known type includes an eye movement photo sensor 132 which is electronically connected to a conventional servo system 140 which includes servo motor 142, power amplifier 144 and a conventional servo controller 146 to which is applied a reference voltage 148. Upon detection of eye movement of a perceiving individual's eye 120 by photo sensor 132, an electrical signal is applied over line 150 to servo controller 146 and amplifier 144 to motor 142. In turn, motor 142 is mechanically coupled (at 159) to the fixer 199 of the system 20 which includes the pivotally mounted mirror 160, the projector 180, and a screen. With the tracker 130 coupled to the fixer 199, the images R1 ... Rn of the record 400 are projected by the projecting means 180, reflected by mirror 160 onto screen 200 under control of the tracker, reflected from spherically shaped reflective screen 200, and focused on the fovea 115 of the perceiver's eye 120. With the tracker 130 and fixer 199, regardless of the position of rotation of the perceiver's eye 120, the retina of the perceiving individual is excited by the same focused images as were seen by the observer. In the case of a non-optical or electronic pixel display, the locus of the image on the display would be adjusted using known means in accordance with the tracking signal normally supplied to mirror 160.

As shown in the figures described above, the sensors and servos are depicted schematically. It will be appreciated, however, that two dimensional tracking (x and y axis) is generally used and separate tracking of left and right eyes may be desirable for stereoscopic presentation although accurate single eye tracking can be extrapolated to both eyes. Z axis tracking, however, is generally not necessary given appropriate optics with sufficient depth of field.

Figure 3:
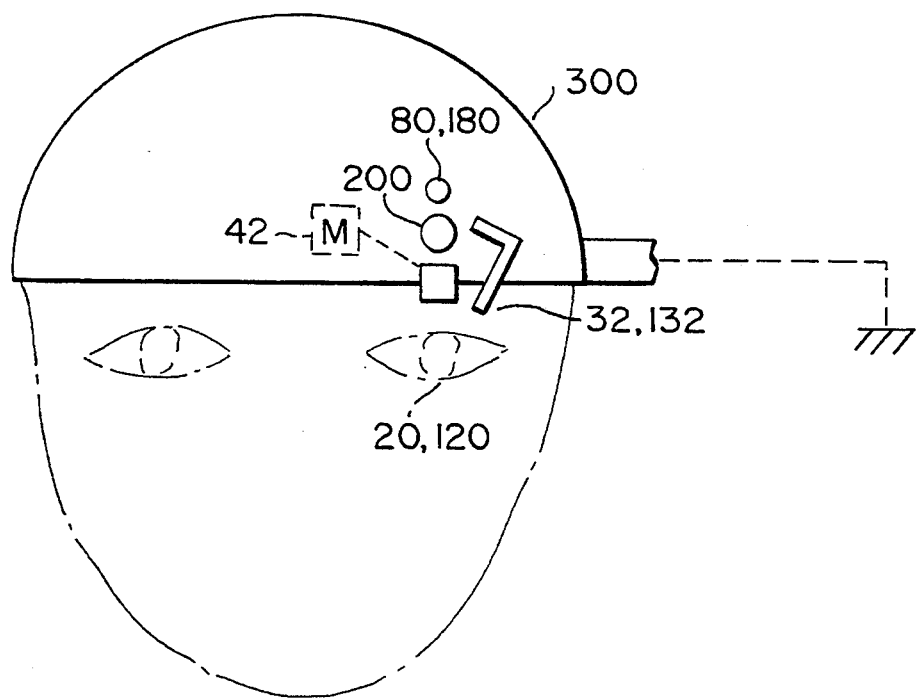
FIG. 3 is an illustration of a particular physical embodiment of the subsystems of FIGS. 1 and 2.

In a particular embodiment of the present invention as seen in FIG. 3, where like numbers represent like components, the components of each subsystem are mounted on a common base fixture or helmet 300 so that the components of a particular subsystem are fixed in position relative to each other and to the wearer; i.e., observer or perceiver. In the device of FIG. 3, the same servo system components and eye movement sensors can be used doubly for both the gazing and perceiving operations. Moreover, in the device of FIG. 3, the display 200 could be made part of a visor using known flat panel display technology. Helmets worn by observer and perceiver in real-time application could be coupled by wireless means.

There has been illustrated and described herein a system for presenting visual information. While the invention was described in terms of the system invention, it will be appreciated that the method invention is related directly thereto and comprises steps such as tracking eyeball movement of the observer, recording the images seen by the observer, and fixing the images seen by the observer on the fovea of the perceiver, etc. Also, while particular embodiments of the invention have been described, it is not intended that the invention be limited thereto, as it is intended that the invention be as broad in scope as the art will allow and that the specification be read likewise. Thus, while particular equipment was disclosed as being preferred, it will be appreciated that other tracking, fixing, and recording equipment could be utilized. Further, while the invention was described as comprising two separate subsystems, it will be appreciated that the subsystems can be partially integrated or completely separate. Where the subsystems are partially integrated, a single helmet or the like shown in FIG. 3 can be utilized, thereby eliminating the need for two different trackers. Where the subsystems are completely separate, it will be appreciated that the locations of the subsystems need not be in proximity to each other. Thus, a recording of the observer's review may be made in a first location for "publication" to perceivers anywhere in the world. The visual information provided is therefore both image records and eye movement information. This information can be provided together or separately in real time or recorded. Moreover, as the nature of this information is understood, it can be enhanced, edited and synthesized by adapting known data manipulation techniques. It will therefore be appreciated by those skilled in the art that yet other modifications could be made to the provided invention without deviating from its spirit and scope as so claimed.

I claim:

1. A system for providing a replica of a pattern of visual information which has excited the retina of an eye of an observing individual observing images to the retina of an eye of a perceiving individual, said system comprising:

a) first tracking means for tracking movement of said eye of said observing individual;

b) imaging means for obtaining a plurality of images corresponding to and simultaneous with said pattern of visual imformation exciting said retina of said observing individual, said imaging means being coupled to and responsive to said first tracking means;

c) image receiving means coupled to said imaging means for receiving said plurality of images obtained by said imaging means and for creating a record of said plurality of images, said record constituting said replica of said pattern of visual information;

d) second tracking means for tracking movement of said eye of said perceiving individual; and e) image fixing means including a projecting means for projecting said record of said plurality of images, said image fixing means being responsive to said second tracking means and optically related to said perceiving individual for presenting to said retina of said eye of said perceiving individual said plurality of images.

2. A system according to claim 1, wherein:
   said first tracking means comprises a first eye movement photo sensor means, a first servo controller coupled to said first eye movement photo sensor means, a first amplifier coupled to said first servo controller, and a first motor coupled to said first amplifier.

3. A system according to claim 2, wherein:
   said image recording means comprises a camera, and said imaging means comprises a first movable mirror means coupled to said motor, said first movable mirror means for providing said camera with said plurality of images.

4. A system according to claim 3, further comprising: discriminator means coupled to said first eye movement photo sensor means and to said image recording means for determining when said eye of said observing individual is fixated and for causing said recording means to record only when said eye of said observing individual is fixated.

5. A system according to claim 4, wherein: said second tracking means comprises a second eye movement photo sensor means, a second servo controller coupled to said second eye movement photo sensor means, a second amplifier coupled to said second servo controller, and a second motor coupled to said second amplifier.

6. A system according to claim 5, wherein: said image fixing means comprises a second movable mirror means coupled to and responsive to said second motor and a reflective screen, wherein said second movable mirror means provides said plurality of images projected by said projecting means to said reflective screen, and said reflective screen focuses said plurality of images on said retina of said perceiver.

7. A system according to claim 3, wherein: said second tracking means comprises a second eye movement photo sensor means, a second servo controller coupled to said second eye movement photo sensor means, a second amplifier coupled to said second servo controller, and a second motor coupled to said second amplifier.

8. A system according to claim 7, wherein: said image fixing means comprises a second movable mirror means coupled to and responsive to said second motor and a reflective screen, wherein said second movable mirror means provides said plurality of images projected by said projecting means to said reflective screen, and said reflective screen focuses said plurality of images on said retina of said perceiver.

9. A system according to claim 1, wherein: said second tracking means comprises an eye movement photo sensor means, a servo controller coupled to said eye movement photo sensor means, an amplifier coupled to said servo controller, and a motor coupled to said amplifier.

10. A system according to claim 9, wherein: said image fixing means comprises a movable mirror means coupled to and responsive to said motor and a reflective screen, wherein said movable mirror means provides said plurality of images projected by said projecting means to said reflective screen, and said reflective screen focuses said plurality of images on said retina of said perceiver.

11. A system for capturing a pattern of visual information which excites the retina of an eye of an observing individual observing images, comprising:
a) tracking means for tracking movement of said eye of said observing individual;
b) imaging means for obtaining a plurality of images corresponding to and simultaneous with said pattern of visual information exciting said retina of said observing individual, said imaging means being coupled to and responsive to said tracking means; and
c) image transmission means coupled to said imaging means for transmitting said plurality of images obtained by said imaging means simultaneous with said pattern of visual information.

12. A system for presenting a pattern of visual information which excites the retina of an eye of a perceiving individual, comprising:
a) tracking means for tracking movement of said eye of said perceiving individual; and
b) image fixing means having image receiving means for receiving a plurality of images and image display means for displaying said plurality of images, said image fixing means being responsive to said tracking means and provided for presenting to said retina of said eye of said perceiving individual said plurality of images.

13. A system for providing a replica of a pattern of visual information which excites the retina of an eye of an observing individual observing images to the retina of an eye of a perceiving individual, said system comprising:
a) first tracking means for tracking movement of said eye of said observing individual;
b) imaging means for obtaining a plurality of images corresponding to and simultaneous with said pattern of visual information exciting said retina of said observing individual, said imaging means being coupled to and responsive to said first tracking means;
c) image transmission means coupled to said imaging means for transmitting said plurality of images obtained by said imaging means constituting said replica of said pattern of visual information;
d) second tracking means for tracking movement of said eye of said perceiving individual; and
e) image fixing means including image display means for displaying said plurality of images, said image display means being coupled to said image transmission means, said image fixing means being responsive to said second tracking means and provided for presenting to said retina of said eye of said perceiving individual said plurality of images.

14. A method for capturing a pattern of visual information which excites the retina of an eye of an observing individual observing images comprising the steps of:
a) tracking movement of said eye of said observing individual;
b) imaging a plurality of images corresponding to and simultaneous with said pattern of visual information exciting said retina of said observing individual in response to said movement of said eye of said observing individual;
c) transmitting said plurality of images obtained during said imaging step, said plurality of images constituting said pattern of visual information.

15. A method for presenting a pattern of visual information which excites the retina of an eye of a perceiving individual, comprising:
a) receiving a plurality of images;
b) displaying said plurality of images;
c) tracking movement of said eye of said perceiving individual; and
d) presenting said plurality of images to said retina of said eye of said perceiving individual in response to said movement of said eye of said perceiving individual.

* * * * *